United States Patent [19]

Anderson et al.

[11] 4,267,363
[45] May 12, 1981

[54] INTERMEDIATES FOR A SEX PHERAMONE FOR YELLOW SCALE

[75] Inventors: Richard J. Anderson; Clive A. Henrick, both of Palo Alto, Calif.

[73] Assignee: Zoecon Corporation, Palo Alto, Calif.

[21] Appl. No.: 918,754

[22] Filed: Jun. 26, 1978

[51] Int. Cl.³ .................. C07C 43/315; C07C 47/198; C07C 69/145; C07C 69/734
[52] U.S. Cl. .................. 560/183; 260/665 R; 424/78; 424/84; 560/240; 560/261; 560/262; 568/483; 568/486; 568/497; 568/598; 568/840; 568/908

[58] Field of Search ................ 560/262, 183; 568/598, 568/497; 260/602; 424/84

[56] References Cited

U.S. PATENT DOCUMENTS

| | | | |
|---|---|---|---|
| 3,919,329 | 11/1975 | Anderson et al. | 568/617 |
| 3,948,814 | 4/1976 | de Ryke | 568/596 |
| 4,014,942 | 3/1977 | Labovitz et al. | 562/262 |
| 4,059,641 | 11/1977 | Mishima et al. | 568/857 |

*Primary Examiner*—Vivian Garner
*Attorney, Agent, or Firm*—Donald W. Erickson

[57] ABSTRACT

Synthesis and intermediates for making an insect pheromone useful in the control of the yellow scale.

9 Claims, No Drawings

INTERMEDIATES FOR A SEX PHERAMONE FOR YELLOW SCALE

This invention relates to the synthesis of the sex pheromone of the yellow scale, *Aonidiella citrina* (Coquillett), and intermediates therefor. The yellow scale is a pest of citrus crops.

The synthesis of the present invention can be outlined as follows:

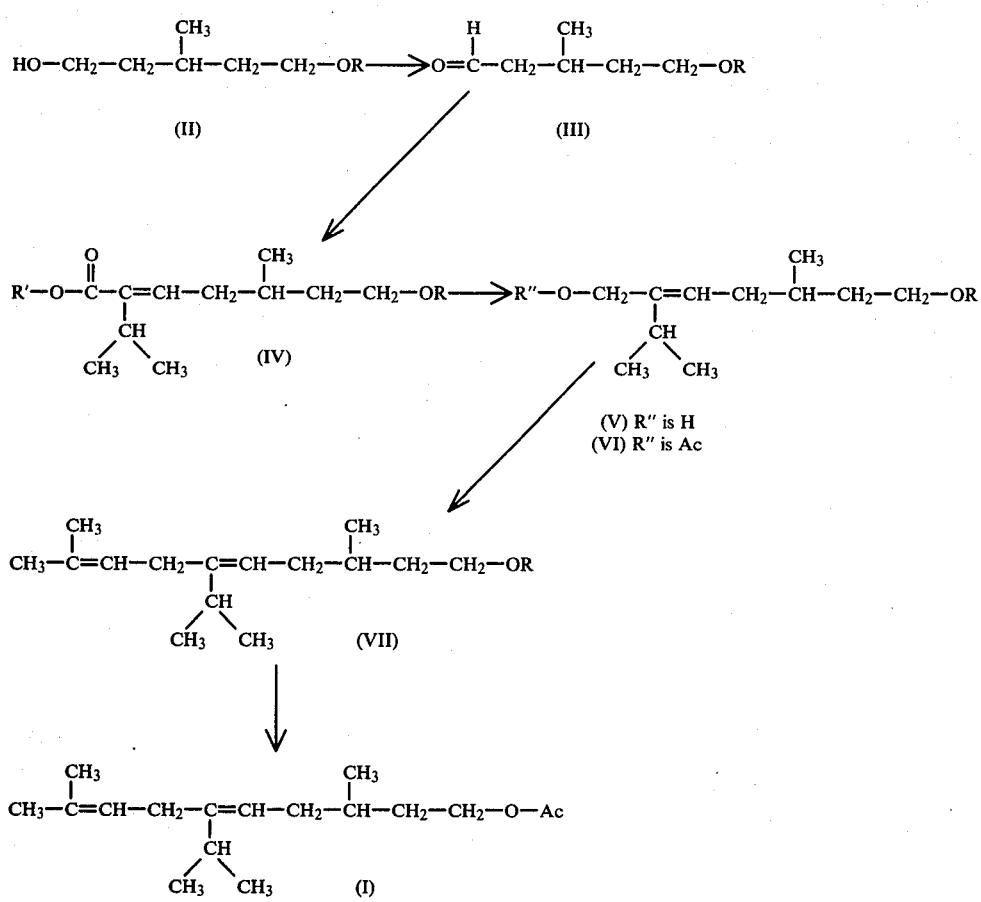

In the practice of the above synthesis, the monomethoxyethoxymethyl ether (II; R is $CH_3OCH_2CH_2OCH_2$-) of 3-methyl-1,5-pentanediol, obtained by treating the diol with one equivalent each of n-butyllithium and methoxyethoxymethyl chloride, is oxidized to the aldehyde (III) using pyridinium chlorochromate and sodium acetate in dichloromethane. Treatment of the aldehyde (III) with the anion of diethyl 1-ethoxycarbonyl-2-methylpropylphosphonate, prepared by isopropylation of the anion of diethyl ethoxycarbonylmethylphosphonate, in tetrahydrofuran, yields a mixture of isomeric esters in a 4:1 ratio. The cis isomer is the major isomer. The mixture of isomers (IV; R' is ethyl) is reduced with diisobutylaluminum hydride in benzene to give the allylic alcohols (V; R" is hydrogen) which are converted to the acetates (VI; R" is acetyl) with excess acetic anhydride and pyridine. The allylic acetates (VI) are reacted with three equivalents of lithium di-2-methyl-1-propenylcuprate, prepared from isobutenyl bromide, in ether at −10°, to yield the desired diene ethers (VII). The ethers (VII) are cleaved using trichloroacetic acid in refluxing ethanol to the corresponding alcohols, which are treated with acetic anhydride in pyridine to yield the diene acetates (I) in a ratio of 4:1 (E:Z). The desired E isomer can be separated by preparative gas liquid chromatography. Alternatively, the mixture of isomers (I) can be used as an attractant for yellow scale, although not as effectively as the E isomer alone.

In an alternate synthesis, the aldehyde (III) is reacted with isobutyltriphenylphosphorane in tetrahydrofuran followed by addition of n-butyllithium and paraformaldehyde to give the allylic alcohol (V; R" is hydrogen) as the cis (Z) isomer only, which is then converted as above to give only the desired trans isomer of the acetate (I).

The yellow scale sex pheromone, (E)-3,9-dimethyl-6-isopropyl-5,8-decadien-1-yl acetate, is useful in conjunction with traps to monitor populations of, or to mass trap, the yellow scale. The amount of pheromone employed per trap is very small. Generally, there is used from about 100 to 1,000 micrograms of pheromone per trap. The sex pheromone is useful also in the confusion technique of insect control which involves releasing an excessive amount of the pheromone, whereby the insects are disoriented and unable to mate. Suitable carriers for the pheromone include rubber and plastic septums, which can then be placed in traps having an adhesive coating. The pheromone may also be blended with a plastic such as polyvinyl chloride for ease of handling and dispensing. Suitable carriers, diluents and traps are described in U.S. Pat. Nos. 3,866,349, 4,034,080 and 4,083,995.

The following examples are provided to illustrate the practice of the present invention. Temperature is given in degrees Centigrade.

EXAMPLE 1

A. To 3.54 g (30 mmol) of 3-methyl-1,5-pentanediol in 30 ml of dry tetrahydrofuran (THF) at 0° was added 19.2 ml (30 mmol) of 1.56 M n-butyllithium. After 30 min, 3.74 g (30 mmol) of β-methoxyethoxymethyl chloride was added and the reaction was stirred overnight. The reaction was poured into ether and water. The aqueous phase was back-extracted twice with ether. Combined ether layers were washed with sat. NaCl solution and were dried over calcium sulfate. The crude product was placed on 1 m×20 cm prep. SiO$_2$ plates which were then developed with 40% ethyl acetate/hexane. Removal of the second least polar band gave the monoether derivative of 3-methyl-1,5-pentanediol (II).

B. To a suspension of 3.2 g (14.7 mmol, 1.7 equiv.) of pyridinium chlorochromate and 246 mg (3 mmol) of sodium acetate in 24 mol of methylene chloride at room temperature under nitrogen was added 1.78 g (8.65 mmol) of the alcohol ether of part A. The dark black suspension was stirred for 2 hr. The reaction mixture was diluted with ether, and then poured through a 1 in×4 in column of Florisil. Solvent was removed to give the aldehyde (III).

C. Sodium hydride (126 mg of 56% NaH in oil dispersion) was washed free of oil with pentane under a nitrogen atmosphere (theo. yield of NaH, 72 mg, 3 mmol) and then suspended in 5 ml of dry THF. To this suspension was added 0.8 g (3 mmol) of diethyl 1-ethoxycarbonyl-2-methylpropylphosphonate. After 45 min, hydrogen evolution had completely ceased, and 0.4 g (2 mmol) of the aldehyde was added. The reaction was quenched with water after 2.5 hr, and worked up with hexane/ether. The organic phase was washed once with sat. NaCl solution and dried over calcium sulfate.

Solvent was removed and the residue (0.8 g) was applied to one 1 m×20 cm prep. SiO$_2$ plate which was developed with 30% ethyl acetate/hexane: Removal of desired band gave the ester (IV; R' is ethyl) in cis/trans ratio of 4:1.

D. To 1.68 g (5.3 mmol) of the ester of part C in 20 ml of dry benzene was added 6.7 ml (12 mmol) of 1.8 M diisobutylaluminum hydride in heptane. After 1.5 hr, an additional 1.5 ml of the reducing agent was added. Saturated ammonium chloride was added to the solution after another hour, and the reaction mixture was poured into ether and water. To facilitate solution of aluminum salts, 2% HCl was added to the workup to attain a final pH of about 4-5. The aqueous fraction was washed several times with additional ether. Combined ether fractions were washed once with sat. NaCl solution and dried (CaSO$_4$). Removal of solvent gave the alcohol (V; R" is hydrogen), cis/trans (4:1).

E. To 100 mg of the alcohol of part D (0.365 mmol) was added 150 μl of acetic anhydride and 250 μl of pyridine. The reaction was stirred overnight at room temperature under a nitrogen atmosphere. Ice was added to the mixture and after 30 min it was poured into ether and 5% HCl. The organic layer was then shaken against 2 M Na$_2$CO$_3$ and sat. NaCl solution and dried (Na$_2$SO$_4$). Removal of solvent gave the allylic acetate (VI; R" is acetyl).

F. To 190 mg (1 mmol) of cuprous iodide in 4 ml of dry ether at −25° under nitrogen was added 3.3 ml of 0.60 M 2-methylpropenyllithium (1.98 mmol) in ether. After 20 min, the solution gave a negative Gilman color test, so 105 mg (0.33 mmol) of allylic acetate of part E in about 1 ml of ether was added. After 4 hr, thin layer chromatography indicated complete reaction. Then sat. aqueous (NH$_4$)$_2$SO$_4$ was added to the mixture. The reaction was poured into a mixture of ether and additional sat. aqueous (NH$_4$)$_2$SO$_4$. The organic phase was washed with water and dried (Na$_2$SO$_4$). Removal of solvent gave crude product which was applied to one 1 m×20 cm prep. SiO$_2$ plate (Rhodamine impregnated), which was then developed with 15% EtOAc/hexane to give the diene ether (VII) in trans,cis ratio of 4:1.

G. A solution of 56 mg (0.18 mmol) of the diene ether of part F and approx. 75 mg of trichloroacetic acid in 5 ml of ethanol and 1 ml of water was heated at 70° under nitrogen for four days. The reaction was worked up by pouring it into ether and 2 M Na$_2$CO$_3$. The organic phase was washed to neutrality (sat. NaCl solution) and dried (Na$_2$SO$_4$). Removal of solvent gave crude product which was purified by prep. thin layer chromatography (Rhodamine impregnated; development solvent, 30% Et$_2$O/hexane) to give the diene alcohol (3,9-dimethyl-6-isopropyl-5,8-decadien-1-ol).

The diene alcohol (27 mg) was dissolved in 100 μl acetic anhydride and 150 μl pyridine, and the reaction was maintained under nitrogen for 3 days. Ice was added to the mixture, and after 30 min it was poured into 5% HCl and ether. The organic phase was then shaken against 2 M aqueous Na$_2$CO$_3$, sat. NaCl and dried (Na$_2$SO$_4$). Solvent was removed and the residue was filtered through a short Florisil column with ether-pentane to give the desired diene acetate (I) in trans,cis ratio of 4:1. The isomers were separated using prep. gas liquid chromatography.

The reagent 2-methylpropenyllithium used in part F above is prepared as follows:

To a solution of 100 g (1 mol) of 3-methyl-2-butenoic acid in 500 ml of CCl$_4$ was added 51.5 ml (160 g, 1 mol) of bromine in 100 ml of CCl$_4$ with ice-bath cooling. Total time of addition: 1.5 hr. As the addition was made, nmr spectra were obtained to determine that the reaction had begun. After stirring overnight (mechanical stirring), the orange suspension was nearly colorless. The white solid was filtered off and washed several times with CCl$_4$. The filtrate volume was reduced by rotoevaporation and a second crop of crystals was collected (62.03 g). These two batches of solid were combined to give 208.5 g of the dibromoacid (2,3-dibromo-3-methylbutanoic acid).

A solution of 125 g (1.2 mol) of sodium carbonate in 500 ml of water was prepared. In this solution was dissolved 208.5 g (0.8 mol) of the dibromoacid and approx. 100–150 ml of water was added. This solution was then heated to 115°–130° and the distillate was collected. After approx. 125 ml of milky distillate had come over, the pot assumed a homogenous clear nature and the distillate also was no longer cloudy. This 125 ml sample was placed in a separatory funnel, and the bottom layer was separated and dried (Na$_2$SO$_4$). The dried material was then distilled to yield 1-bromo-2-methyl-1-propene, b.p. 86°–87°.

Lithium wire-1% Na (6.5 cm, approx. 280 mg, 40 mmol) was cut into small pieces into 10 ml of dry diethyl ether under an argon atmosphere, and the suspension cooled to 0°. Then about 0.7 g of 1-bromo-2-methyl-1-propene was added. The reaction began almost immediately, and an additional 2.0 g (total 2.7 g, 20 mmol) of the bromide was added in several portions. After about 1 hr, another 15 ml of ether was added to the reaction, and after several more hours all of the lithium had been consumed. Titration of a sample gave a molarity of 0.67 M.

EXAMPLE 2

To a suspension of 800 mg (2 mmol) of isobutyl triphenylphosphonium bromide in 8 ml of THF at −10°, under nitrogen atmosphere, was added 1.3 ml of 1.53 M n-butyllithium (2 mmol). After one hour (negative Gilman color test), the orange solution was cooled to −78° and 408 mg (2 mmol) of aldehyde (III) in several ml of THF was added dropwise. The light yellow colored suspension was stirred at −70° to −78° for one hour. An aliquot removed after that time showed no remaining aldehyde by thin layer chromatography. Then another 1.3 ml of n-butyllithium was added and the solution held at −78° for one hour. The reaction mixture (red-orange in color) was then slowly warmed to −40° over 1.5 hour. The reaction was further warmed to 0° over another 30 minutes and then 140 mg (4.7 mmol) of dry paraformaldehyde was added. The temperature was maintained at 0° for one hour and then brought to room temperature. The reaction mixture was stirred overnight and then several ml of water was added. After an hour, the reaction was poured into a mixture of ether and water. The organic phase was separated, washed to neutrality with sat. NaCl solution and dried (Na2SO4). Solvent was removed and the residue applied to two 1 m×20 cm prep. silica gel plates (Rhodamine impregnated) which were developed with 50% ethyl acetate/hexane. The region of $R_f$ about 0.1–0.2 was removed to yield cis alcohol (V; R″ is hydrogen).

In an alternative procedure of the above reaction, the step of adding dry paraformaldehyde can be replaced by passing excess gaseous formaldehyde (by cracking paraformaldehyde) into the reaction mixture.

What is claimed is:

1. A compound selected from those of the following formulas (III), (IV), (V), (VI) and (VII):

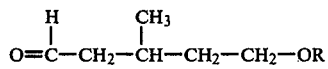

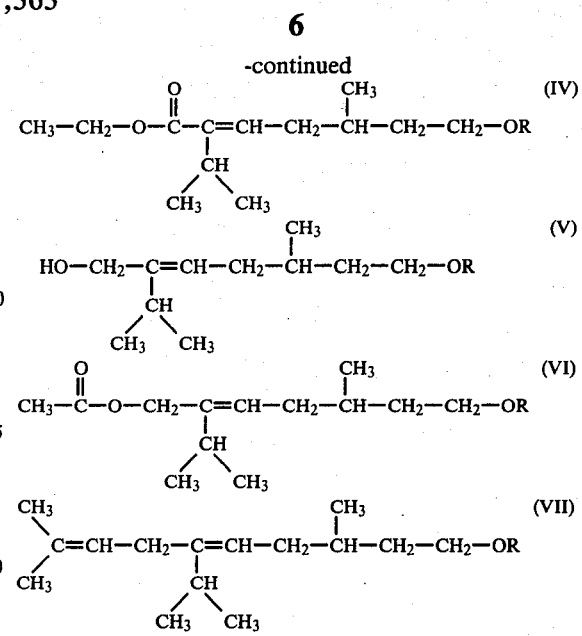

wherein R is β-methoxyethoxymethyl.

2. The compound,

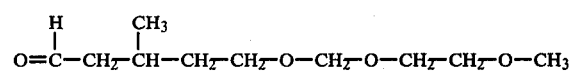

according to claim 1.

3. A compound,

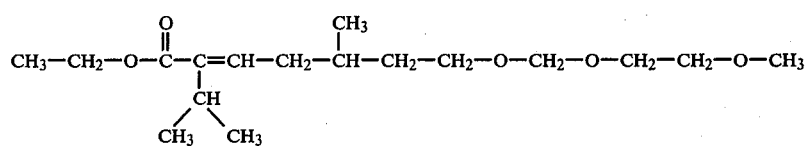

according to claim 1.

4. A compound of the formula,

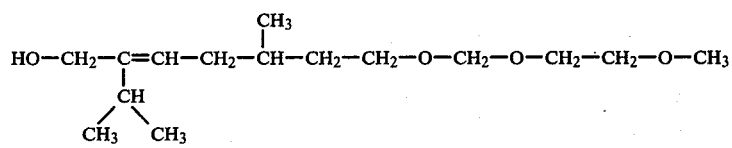

and a mixture of the cis and trans isomers of said compound in a ratio of cis isomer to trans isomer of 4:1.

5. A mixture of the cis and trans isomers of the compound of claim 4 in a ratio of cis isomer to trans isomer of 4:1.

6. The cis isomer of the compound of claim 4.

7. A compound of the formula

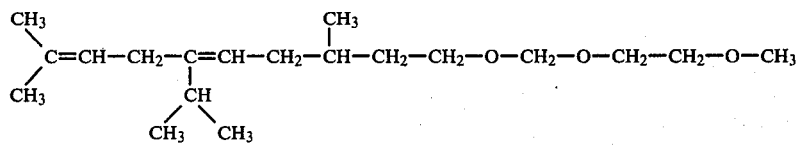

and a mixture of the trans and cis isomers of said compound in a ratio of trans isomer to cis isomer of 4:1.

8. A mixture of the trans and cis isomers of the compound of claim 7 in a ratio of trans isomer to cis isomer of 4:1.

9. The trans isomer of the compound of claim 7.

* * * * *